United States Patent [19]

Partyka et al.

[11] 4,001,237
[45] Jan. 4, 1977

[54] OXAZOLE, ISOXAZOLE, THIAZOLE AND ISOTHIAZOLE AMIDES

[75] Inventors: Richard Anthony Partyka, Liverpool; Ronnie Ray Crenshaw, Dewitt, both of N.Y.

[73] Assignee: Bristol-Myers Company, New York, N.Y.

[22] Filed: Feb. 18, 1976

[21] Appl. No.: 658,961

[52] U.S. Cl. .............. 260/256.4 B; 260/256.4 Q; 424/251

[51] Int. Cl.² ...................... C07D 239/84

[58] Field of Search ............ 260/256.4 Q, 256.4 B

[56] References Cited

UNITED STATES PATENTS 3,511,836  5/1970  Hess ........................ 260/256.4 Q
3,935,213  1/1976  Hess ........................ 260/256.4 Q

*Primary Examiner*—Paul M. Coughlan, Jr.
*Attorney, Agent, or Firm*—Robert E. Havranek

[57] ABSTRACT

Compounds having the formula

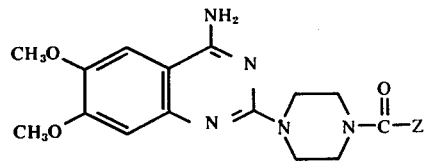

wherein Z is a substituted or unsubstituted oxazole, isoxazole, thiazole or isothiazole group are potent antihypertensive drugs which have generally less α-adrenergic blocking activity than does 2-[4-(2-furoyl)-piperazin-1-yl]-4-amino-6,7-dimethoxy-quinazoline which is a known potent antihypertensive drug.

12 Claims, No Drawings

OXAZOLE, ISOXAZOLE, THIAZOLE AND ISOTHIAZOLE AMIDES

BACKGROUND OF THE INVENTION

1. Field of the Invention

This invention relates to novel nitrogenous containing heterocuclic carbonyl piperazinyl quinazolines which are potent antihypertensive drugs.

2. Description of the Prior Art

U.S. Pat. Nos. 3,511,386; 3,635,979; and 3,663,706 disclose several 4-amino-6,7-dimethoxy-2-[4-(heterocyclic-2-carbonyl)-piperazin-1-yl] quanazolines. One of these compounds, i.e., 2-[4-(2-furoyl)-piperazin-1-yl]-4-amino-6,7-dimethoxyquinazoline described in Example LXXII of these patents is a clinically useful antihypertensive agent and is marketed as such in many countries of the world under the generic name prazosin. It is well established that the antihypertensive efficacy of prazosin results from a dual mechanism of action: (i) a direct peripheral vasodilatation effect on vascular smooth muscle, and (ii) a functional peripheral α-adrenergic receptor blockade, H. Adriaensen, The Practitioner, 214, 268 (1975); Mroczek, et al., Current Therapeutic Research, 16, 769 (1974); Scriabine, et al., Experientia, 24, 1150 (1968); Constantine, et al., "Hypertension: Mechanisms and Management", ed. by Onesti, Kim and Moyer; Grune and Stratton, 1937 pp. 429–44; and Zacest, Med. J. of Austral. Special Supplement, 1,4 (1975). Although initial clinical assessments on prazosin indicated an almost complete absence of side effects, recent reports have revealed severe adverse reactions of postural hypotension in some patients, Bendall, et al., Brit. Med. J., 727 (June 28, 1975); Rees, Brit. Med. J., 593 (Sept. 6, 1975); Gabriel, et al., The Lancet, 1095 (May 10, 1975); and Bloom et al., Current Therapeutic Research, 18, 144 (1975). It is generally felt that this type of side effect results from the α-blockade component of prazosin. Indeed, it has been stated by R. Zacest in the Med. J. of Austral., Special Supplement, 1, 4 (1975) that "if the alpha adrenergic 'blocking' activity does prove to be significant with high doses it may lead to postural hypotension".

U.S. Pat. Nos. 3,669,968 and 3,769,286 cover trialkoxyquinazolines, such as those having the formula:

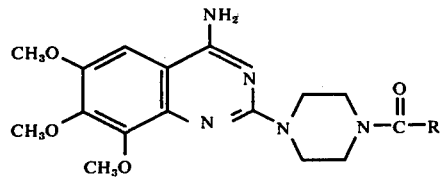

wherein R may be a number of different groups including furyl and thienyl. These patents claim to have certain advantages over the corresponding 6,7-dialkoxy coupounds such as those disclosed in the patents previously discussed. Thus, it is stated that such compounds "have a more favorble pharmacological profice (e.g., they are non-adrenolytic in dogs) and possess greatly improved solubility characteristics (particularly in water) as contrasted to the corresponding 6,7-dialkoxy compounds reported in the prior art". One of the compounds disclosed in these patents is known by the generic name trimazosin and has the formula:

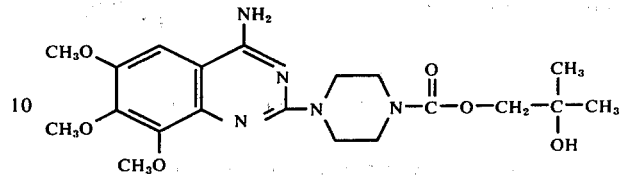

Trimazosin is reported to be active in humans as an antihypertensive agent, DeGuia, et al., Current Therapeutic Research, 15, 339 (1973); Vlachakis et al., Current Therapeutic Research, 17, 564 (1975). However, it is a much weaker drug than prazosin, the respective clinical daily dose ranges being approximately 150 to 500 mg. for trimazosin as compared to 1.5 to 15 mg. for prazosin. Trimazosin is therefore 100-fold weaker than prazosin at the lower end of the dosage range.

U.S. Pat. Nos. 3,517,005; 3,594,480; and 3,812,127 describe certain piperazinyl quinazolines having both broncho-dilator and antihypertensive activity, e.g., a compound having the formula:

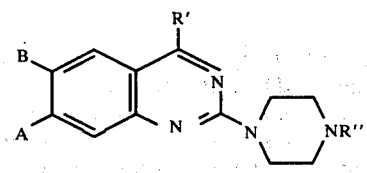

wherein A and B may each be alkoxy, etc., $R^1$ may be hydrogen or alkyl and $R^2$ may be hydrogen or a radical such as alkyl, benzoyl, etc.

U.S. Pat. No. 3,920,636 describes homopiperazino quinazolines as antihypertensive agents, e.g., the compound:

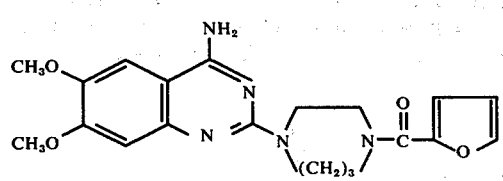

U.S. Pat. No. 3,780,040 discloses compounds useful as antihypertensive agents such as the compound:

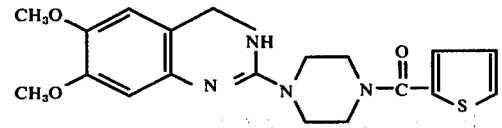

Netherlands application No. 72 06,067 (CA, 78, 72180s) describes a process for preparing aminoquinazolines, such as prazosin, by treating the corresponding o-aminobenzonitrile in the pesence of phenyl lithium according to the following mechanism:

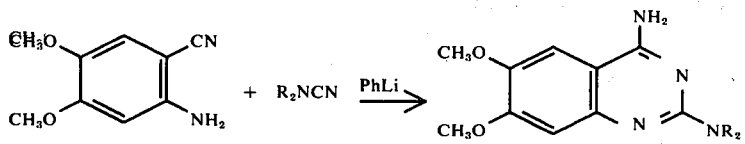

SUMMARY OF THE INVENTION

Compounds having the formula:

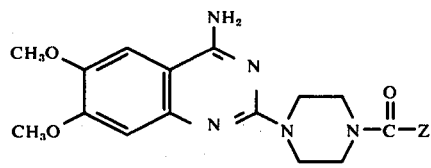

wherein Z is either the radical

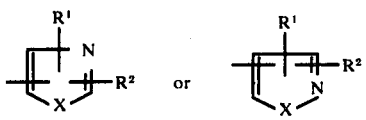

in which X is either oxygen of sulfur and $R^1$ and $R^2$ may be the same or different and are selected from the group consisting of hydrogen, (lower)alkyl having from 1 to 6 carbon atoms, (lower)alkoxy having from 1 to 6 carbon atoms and (lower)alkylthio having from 1 to 6 carbon atoms and pharmaceutically acceptable acid addition salts thereof, possess antihypertensive potency comparable to prazosin but have generally less of the peripheral α-adrenergic blocking properties shown by prazosin.

COMPLETE DISCLOSURE

The compounds of this invention may be prepared by several different methods. The preferred method, which will be exemplified in the examples appearing hereinafter, invovles the following reaction:

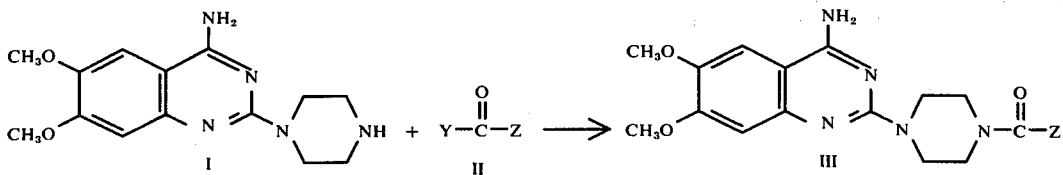

wherein Z is either the radical

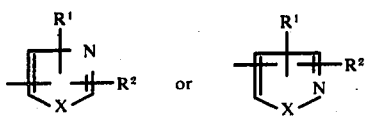

in which X is either oxygen or sulfur and $R^1$ and $R^2$ may be the same or different and are selected from the group consisting of hydrogen, (lower)alkyl having from 1 to 6 carbon atoms, (lower)alkoxy having from 1 to 6 carbon atoms and (lower)alkylthio having from 1 to 6 carbon atoms and Y is a carbonyl activating group of the type typically used in amidation reactions, e.g., halo, azido, ethoxycarbonyloxy, 1-imidazo, etc. The preparation of compound I will be described hereinafter. The reaction of compound I with compound II is preferably conducted in an inert solvent such as dioxane, chloroform, methylene chloride, glyme and the like at room temperature, and/or with heating at reflux.

The process for the preparation of the compounds of this invention is also new and novel. The preferred process for preparing compounds having the formula

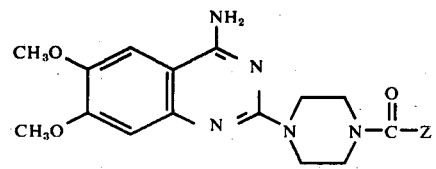

wherein Z is the same as previously described comprises acylating a compound having the formula

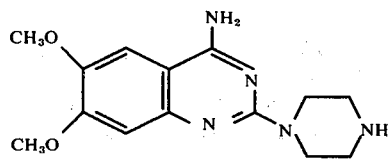

with a compound having the formula

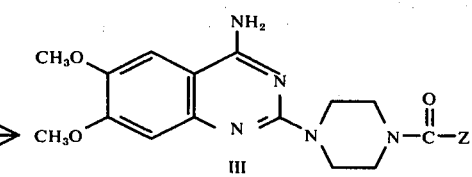

wherein Y and Z are the same as previously described. In a preferred embodiment, the reaction is conducted in the presence of an inert solvent such as dioxane, methylene chloride, glyme and the like.

A second method which may be employed to prepare the compounds of this invention is illustrated by the following equation.

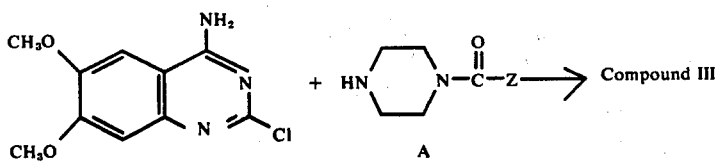

wherein Z is the same as previously described.

Another method for the preparation of the compounds of this invention involves the following reaction sequence:

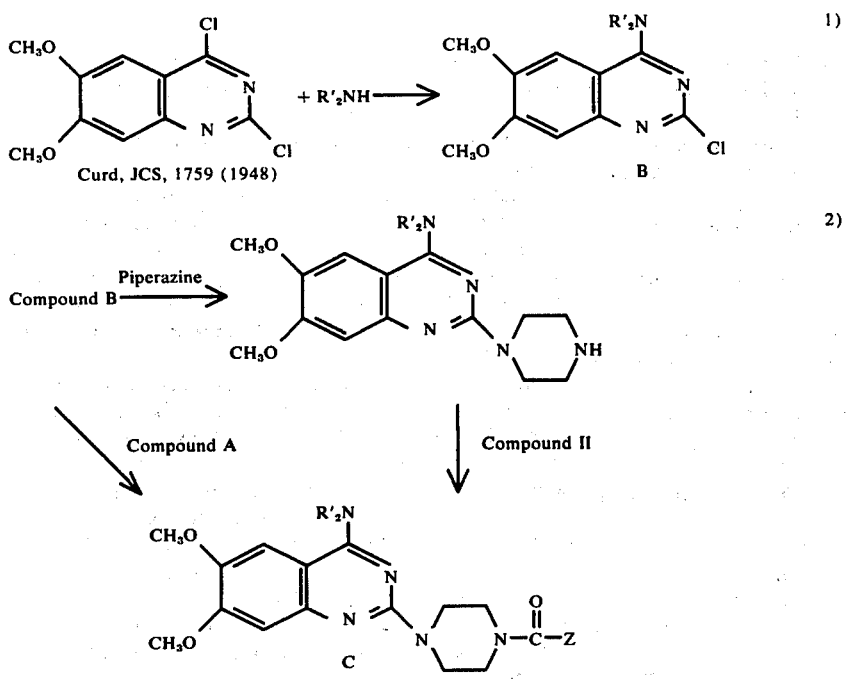

wherein R'$_2$ is a conventional amine protecting group (e.g., a t-butoxycarbonyl group) and wherein Z is the same as previously described. The amine protecting group may then be removed from compound C by conventional means to provide the desired product; compound III.

Another procedure for the preparation of compounds of this invention is illustrated by the following reaction sequence:

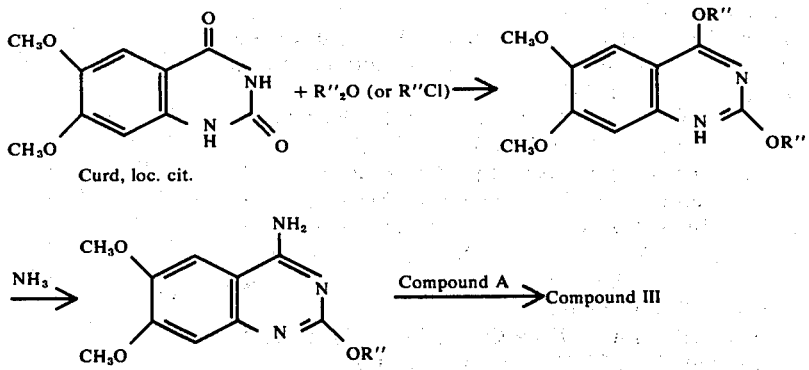

wherein R'' is a group such as F$_3$CC(O), CH$_3$SO$_2$, F$_3$CSO$_2$, aryl SO$_2$, etc.

Still another method for the preparation of compounds of this invention is illustrated in the following reaction sequence:

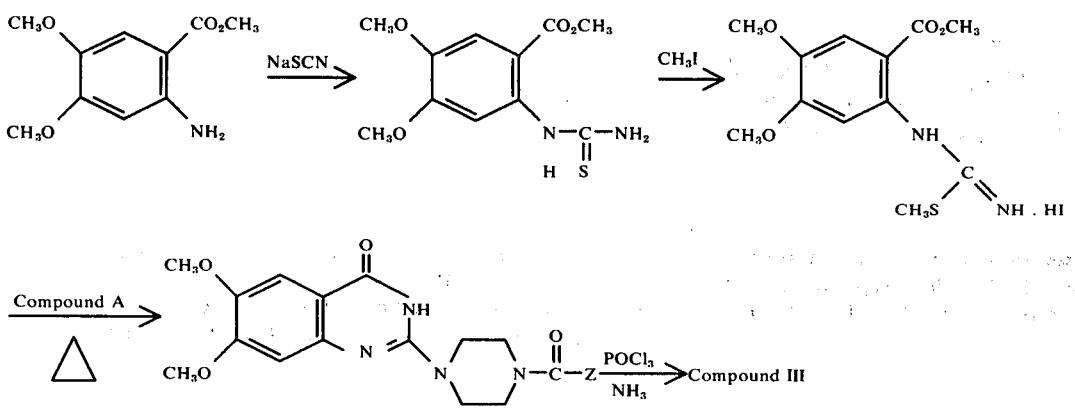

wherein Z is the same as previously described.

In the following examples, compound II is used in the form of its acid chloride, i.e., Y is Cl. The acid chlorides were prepared from the corresponding heterocyclic acids or their metal salts by treatment with either thionyl chloride or oxalyl chloride.

The following experiment shows the preparation of compound I:

4-Amino-6,7-dimethoxy-2-(1-piperazinyl)quinazoline (I)

Piperazine hydrobromide (168.0 g., 1.006 mole) was added to a suspension of 4-amino-2-chloro-6,7-dimethoxyquinazoline (241.0 g., 1.006 mole) in 2-methoxyethanol (3.6 l.) and the mixture was stirred at reflux for 1.25 hours. The precipitate was separated by filtration, washed with hot 2-methoxyethanol and dried. The material then was added to a stirred solution of sodium hydroxide (81.0 g., 2.01 mole) in water (3 l.) and the mixture was heated to 75° C. The mixture then was cooled to 40° C., filtered, and the insoluble precipitate washed with water and dried. The material was triturated under refluxing absolute ethanol (6.0 l.) and the mixture was filtered. The filtrate was evaporated to dryness to yield the title compound, 180.0 g. (62%), m.p. 224°–228° C.

Compound I can exist in two polymorphic forms. In an earlier experiment similar to that just described with the exception that an excess of piperazine hydrobromide was used, a water soluable form (Isomorph A) of Compound I having a m.p. of 224°–228° C. was obtained. This product was recrystallized from nitromethane to give an analytical sample of Isomorph A having a m.p. of 227°–229° C.

Anal. Calcd for $C_{14}H_{19}N_5O_2$: C, 58.12; H, 6.62; N, 24.20. Found: C, 58.23; H, 6.75; N, 24.22.

A 200 mg. sample of Isomorph A was dissolved in 10 ml. of water at 20° C. The solution was heated at 60° C. for 3 minutes, then cooled to 35° C. and filtered. The precipitate (157 mg.), m.p. 228°–230° C. would not redissolve in boiling water. This product was termed Isomorph B of Compound I.

Anal. Calcd for $C_{14}H_{19}N_5O_2$: C, 58.12; H, 6.62; N, 24.20. Found: C, 57.77 H, 6.54; N, 24.05.

The infrared spectra of Isomorph A and Isomorph B of Compound I show distinct differences. The product obtained from the large scale experiment previously described is Isomorph B.

As previously discussed, compounds of this invention are valuable antihypertensive agents, possessing comparable antihypertensive potency to prazosin. However, they have generally less of the peripheral α-adrenergic blocking properties shown by prazosin. Moreover, some of the compounds of this invention have a lowered potential for severe hypotension which is experienced with some antihypertensive drugs because of a "plateauing" dose response effect present in some of the compounds described herein. This effect refers to those instances in which a maximum blood pressure lowering effect is seen at 3 mg./kg. which could not be increased, at higher doses; c.f. the results of tests conducted on the compounds of Examples 10 and 13 described hereinafter.

The compounds of this invention may be used in the form of the free base or in the form of pharmaceutically acceptable acid salts thereof, such as salts of sulfuric acid, hydrochloric acid, succinic acid, tartaric acid, benzoic acid, etc. The compounds may be administered orally or parenterally with oral administration being preferred. Generally, dosages will range from 0.1 to 10 mg. 3 to 4 times per day per human adult. As is usual in antihypertensive therapy, the particular optimum dosage may vary considerably depending upon the sensitivity of the patient to the drug and the severity of the hypertension.

EXAMPLES

EXAMPLE 1

4-Amino-6,7-dimethyoxy-2-[4-(isoxazole-5-carbonyl)-piperazine-1-yl]quinazoline Hydrochloride A solution of isoxazole-5-carbonyl chloride (1.33 g., 0.01 mole) in dioxane was added to a solution at 30° C. of 4-amino-6,7-dimethoxy-2-(1-piperazinyl)quinazoline (2.94 g., 0.01 mole) in dioxane. The mixture was stirred at reflux for three minutes, then at room temperature for 16 hours. Filtration gave the title compound (4.02 g., 94% yield). Recrystallization from aqueous methanol gave a product having a m.p. of 270° C. with decomposition.

Anal. Calcd. for $C_{18}H_{20}N_6O_4 \cdot HCl$: C, 51.37; H, 5.03; Cl, 8.42; N, 19.97. Found C, 50.86; H, 4.65; Cl, 8.52; N, 19.81 (corrected for 4.30% $H_2O$).

EXAMPLE 2

4-Amino-6,7-dimethoxy-2-[4-(isoxazole-3-carbonyl)-piperazin-1-yl]quinazoline Hydrochloride A solution of isoxazole-3-carbonyl chloride (0.753 g., 0.0057 mole) in dioxane (20 ml.) was added to a solution of 4-amino-6,7-diimethoxy-2-(1-piperazinyl)-quinazoline (1.66 g., 0.0057 mole) in dioxane (60 ml.).

The mixture was stirred at reflux for 30 minutes, then at room temperature for 64 hours. Filtration gave the title compound which was recrystallized from methanol (1.81 g., 75% yield). The product had a m.p. of 268–273° C. with decomposition.

Anal. Calcd. for $C_{18}H_{20}N_6O_4 \cdot HCl$: C, 51.37; H, 5.03; Cl, 8.42; N, 19.97, Found: C, 50.04; H, 4.86; Cl, 8.66; N, 19.57 (corrected for 3.11% $H_2O$).

EXAMPLE 3

4-Amino-6,7-dimethoxy-2-[4-(isoxazole-4-carbonyl)-piperazin-1-yl]quinazoline Hydrochloride A solution of isoxazole-4-carbonyl chloride (1.06 g., 8.08 mmole) in dioxane (8 ml.) was added to a solution of 4-amino-6,7-dimethoxy-2-(1-piperazinyl)quinazoline (2.34 g., 8.08 mmole) in dioxane (200 ml.). The mixture was stirred at room temperature for 20 hours. Filtration gave the title compound, which, after recrystallization from methanol, had a m.p. of 225°–260° C. with decomposition.

Anal. Calcd. for $C_{18}H_{20}N_6O_4 \cdot HCl$: C, 51.37; H, 5.03; Cl, 8.42; N, 19.97. Found: C, 51.37; H, 4.95; Cl, 8.34; N, 19.95 (corrected for 1.63% $H_2O$).

EXAMPLE 4

4-Amino-6,7-dimethoxy-2-[4-(5-methylisoxazole-3-carbonyl)piperazin-1-yl]quinazoline Hydrochloride A solution of 5-methylisoxazole-3-carbonyl chloride (0.41 g., 2.83 mmole) in dioxane was added to a solution of 4-amino-6,7-dimethoxy-2-(1-piperazinyl) quinazoline (0.82 g., 2.83 mmole) in dioxane. The mixture was treated as described in the previous example to give the title compound having a m.p. of 271°–273° C. with decomposition.

Anal. Calcd. for $C_{19}H_{22}N_6O_4 \cdot HCl \cdot H_2O$: C, 50.38; H, 5.56; N, 18.56; $H_2O$, 3.92. Found: C, 50.58; H, 5.40; N, 18.86; $H_2O$, 3.72.

EXAMPLE 5

4-Amino-6,7-dimethoxy-2-[4-(3-methylisoxazole-4-carbonyl)piperazin-1-yl]quinazoline Hydrochloride A solution of 3-methylisoxazole-4-carbonyl chloride (1.01 g., 6.9 mmole) in dioxane and 4-amino-6,7-dimethoxy-2-(1-piperazinyl)quinazoline (2.00 g., 6.9 mmole) in dioxane was stirred under reflux for 15 hours, then worked up as described in Example 1. The title compound after recrystallization from methanol had a m.p. of 300°–301° C. with decomposition.

Anal. Calcd. for $C_{19}H_{22}N_6O_4 \cdot HCl$: C, 52.47; H, 5.33; N, 19.33. Found: C, 52.62; H, 5.31; N, 19.12 (corrected for 1.13% $H_2O$).

EXAMPLE 6

4-Amino-6,7-dimethoxy-2-[4-(3-methylisoxazole-5-carbonyl)piperazin-1-yl]quinazoline Hydrochloride A solution of 3-methylisoxazole-5-carbonyl chloride (0.73 g., 5.02 mmole) in dioxane was added to a solution of 4-amino-6,7-dimethoxy-2-(1-piperazinyl) quinazoline (1.45 g., 5.02 mmole) in dioxane. The mixture was heated briefly, then was stirred at 20° C. for 2.5 hours. Workup as in Example 1 gave the title compound having a m.p. of 263°–264° C. with decomposition.

Anal. Calcd. for $C_{19}H_{22}N_6O_4 \cdot HCl$: C, 52.47; H, 5.33; Cl, 8.15; N, 19.33. Found: C, 51.82; H, 5.04; Cl, 8.36; N, 19.46 (corrected for 4.82% $H_2O$).

EXAMPLE 7

4-Amino-6,7-dimethoxy-2-[4-(oxazole-4-carbonyl)-piperazin-1-yl]quinazoline Hydrochloride A solution of oxazole-4-carbonyl chloride (0.73 g., 5.53 mmole) in dioxane was added to a solution of 4-amino-6,7-dimethoxy-2-(1-piperazinyl)quinazoline (1.60 g., 5.53 mmole) in dioxane. The mixture was heated at reflux for 0.5 hour, then was stirred at 20° C. for 64 hours. Filtration gave the title compound having a m.p. of 291°–294° C. with decomposition after recrystallization from acqueous ethanol.

Anal. Calcd. for $C_{18}H_{20}N_6O_4 \cdot HCl \cdot H_2O$: C, 49.26; H, 5.28; Cl, 8.08; N, 19.15. Found: C, 48.92; H, 4.83; Cl, 8.33; N, 18.94.

EXAMPLE 8

4-Amino-6,7-dimethoxy-2-[4-(2-methyloxazole-4-carbonyl)piperazin-1-yl]quinazoline Hydrochloride A solution of 2-methyloxazole-4-carbonyl chloride (1.01 g., 6.9 mmole) in dioxane was added to a solution of 4-amino-6,7-dimethoxy-2-(1-piperazinyl)quinazoline (2.00 g., 6.9 mmole) in dioxane. The mixture was heated at reflux for 2 hours. Filtration gave the title compound having a m.p. of 278°–280° C. with decomposition after recrystallization from methanol.

Anal. Calcd. for $C_{19}H_{22}N_6O_4 \cdot HCl$: C, 52.47; H, 5.33; N, 19.33. Found: C, 52.08; H, 5.43; N, 18.89 (corrected for moisture).

EXAMPLE 9

4-Amino-6,7-dimethoxy-2-[4-(4-methyloxazole-5-carbonyl)piperazin-1-yl]quinazoline Hydrochloride The title compound was prepared from 4-methyloxazole-5-carbonyl chloride (0.85 g.) and 4-amino-6,7-dimethoxy-2-(1-piperazinyl)quinazoline (1.68 g.) following the procedure of Example 1. The product had a m.p. of 283.5°–288° C. with decomposition.

Anal. Calcd. for $C_{19}H_{22}N_6O_4 \cdot HCl$: C, 52.48; H, 5.33; Cl, 8.15; N, 19.33. Found C, 52,19; H, 4.94; Cl, 8.13; N, 19.05 (corrected for 1.59% $H_2O$).

EXAMPLE 10

4-Amino-6,7-dimethoxy-2-[4-(isothiazole-4-carbonyl)piperazin-1-yl]quinazoline Hydrochloride The title compound was prepared from isothiazole-4-carbonyl chloride (1.01 g.) and 4-amino-6,7-dimethoxy-2-(1-piperazinyl)quinazoline (1.99 g.) following previously described procedures. The product had a m.p. of 286°–287° C. with decomposition.

Anal. Calcd. for $C_{18}H_{20}N_6O_3S \cdot HCl$: C, 49.48; H, 4.84; Cl, 8.11; N, 19.23; S, 7.34. Found: C, 49.29; H, 4.81; Cl, 8.19; N, 19.27; S, 7.23 (corrected for 0.93% $H_2O$).

EXAMPLE 11

4-Amino-6,7-dimethoxy-2-[4-thiazole-2-carbonyl)piperazin-1-yl]quinazoline Hydrochloride The title compound was prepared from thiazole-2-carbonyl chloride (0.79 g.) and 4-amino-6,7-dimethoxy-2-(1-piperazinyl)quinazoline (1.54 g.) following previously described procedures. The product had a m.p. of 273°–276° C. with decomposition.

Anal. Calcd. for $C_{18}H_{20}N_6O_3S \cdot HCl$: C, 49.48; H, 4.84; N, 19.23. Found: C, 48.68; H, 4.62; N, 18.87 corrected for 4.19 % $H_2O$).

EXAMPLE 12

4-Amino-6,7-dimethoxy-2-[4-(thiazole-4-carbonyl)-piperazin-1-yl])quinazoline Hydrochloride The title compound was prepared from thiazole-4-carbonyl chloride (1.02 g.) and 4-amino-6,7-dimethyoxy-2-(1-piperazinyl)quinazoline (2.00 g.) following previously described procedures. The product had a m.p. of 274°–277° C. with decomposition.

Anal. Calcd. for $C_{18}H_{20}N_6O_3S \cdot HCl$: C, 49.48; H, 4.48; N, 19.24. Found: C, 49.11; H, 4.69; N, 19.31 (corrected for 4.47% $H_2O$).

EXAMPLE 13

4-Amino-6,7-dimethyoxy-2-[4-(2-methylthiazole-4-carbonyl)piperazin-1-yl]quinazoline Hydrochloride The title compound was prepared from 2-methyl-thiazole-4-carbonyl chloride (0.49 g.) and 4-amino-6,7-dimethyoxy-2-(1-piperazinyl)quinazoline (0.87 g.) following previously described procedures. The product had a m.p. of 260°–263° C. with decomposition.

Anal. Calcd. for $C_{19}H_{22}N_6O_3S \cdot HCl$: C, 50.60; H, 5.14; N, 18.64. Found: C, 50.88; H, 4.96; N, 18.67 (corrected for 2.88 % $H_2O$).

EXAMPLE 14

4-Amino-6,7-dimethoxy-2-[4-(thiazole-5-carbonyl)-piperazin-1-yl]quinazoline Hydrochloride The title compound was prepared from thiazole-5-carbonyl chloride (0.77 g.) and 4-amino-6,7-dimethoxy-2-(1-piperazinyl)quinazoline (1.51 g.) following previously described procedures. The product had a m.p. of 280°–281° C. with decomposition.

Anal. Calcd. for $C_{18}H_{20}N_6O_3S \cdot HCl$: C, 49.48; H, 4.84; Cl, 8.11 N, 19.23; S, 7.34. Found: C, 49.22; H, 5.19; Cl, 8.31; N, 19.49; S, 6.79 (corrected for 2.63% $H_2O$).

EXAMPLE 15

4-Amino-6,7-dimethyoxy-2-[4-(2-methylthiazole-5-carbonyl)piperazin-1-yl]quinazoline Hydrochloride The title compound was prepared from 2-methyl-thiazole-5-carbonyl chloride (0.42 g.) and 4-amino-6,7-dimethoxy-2-(1-piperazinyl)quinazoline (0.75 g.) following previously described procedures. The product had a m.p. of 294°–297° C. with decomposition.

Anal. Calcd. for $C_{19}H_{22}N_6O_3S \cdot HCl$: C, 50.60; H, 5.14; N, 18.64. Found: C, 50.60; H, 4.95; N, 18.50 (corrected for 1.96 % $H_2O$).

EXAMPLE 16

4-Amino-6,7-dimethoxy-2-[4-(4-methylthiazole-5-carbonyl)piperazin-1-yl]quinazoline Hydrochloride The title compound was prepared from 4-methyl-thiazole-5-carbonyl chloride (1.1 g.) and 4-amino-6,7-dimethyoxy-2-(1-piperazinyl)quinoazoline (2.0 g.) following previously described procedures. The product had a m.p. of 293°–295° C. with decomposition.

Anal. Calcd. for $C_{19}H_{22}N_6O_3S \cdot HCl$: C, 50.60; H, 5.14; N, 18.64. Found: C, 50.47; H, 4.78; N, 18.43 corrected for 4.72% $H_2O$).

To determine the efficacy of the compounds of this invention as antihypertensive agents, tests were conducted comparing the products of the foregoing examples to prazosin. The results of these tests are set forth in the following table. As shown in this table, the products obtained in the foregoing examples are of comparable antihypertensive potency to prazosin, but have generally less of the periperal α-adrenergic blocking properties shown by prazosin. The compounds described and claimed in this application thus represent a significant and unexpected advance in the continuing quest for potent antihypertensive drugs.

In the following table, antihypertensive acitvity was determined by oral administration to spontaneous hypertensive rats, and the in vitro and in vivo α-adrenergic receptor blocking effect was determined by tests described following the table. In the in vitro test, the inhibition by the test drug of norepinephrine induced contractions of rat seminal vesicles was measured; and in the in vivo test, the inhibition by the test drug of norepinephrine induced pressor responses in anesthetized dogs was measured. The in vivo tests were conducted using intravenous administration, each compound being assayed in 4 dogs with 2 dose response results in each dog.

TABLE

| Example | Antihypertensive Activity | | α-Adrenergic Receptor Blocking Effect | |
|---|---|---|---|---|
| | Dose mg/kg | % Blood Pressure Change | In Vitro Activity Ratio | In Vivo Activity Ratio |
| Prazosin (Reference Drug) | 10 | −42 | 1.0 | 1.0 |
| | 3 | −29 | | |
| | 1 | −14 | | |
| 1 | 10 | −35 | 0.11 | 0.18 |
| | 3 | −26 | | |
| | 1 | −15 | | |
| 2 | 10 | −32 | | |
| | 3 | −26 | | |
| | 1 | −12 | | |
| 3 | 10 | −35 | 0.92 | |
| | 3 | −23 | | |
| | 1 | −13 | | |
| 4 | 10 | −41 | 0 | 0.24 |
| | 3 | −18 | | |
| | 1 | −14 | | |
| 5 | 10 | −33 | 0.30 | 0.18 |
| | 3 | −29 | | |
| | 1 | −17 | | |
| 6 | 10 | −37 | 0.25 | |
| | 3 | −21 | | |
| | 1 | −18 | | |
| 7 | 10 | −45 | 0.6 | 1.22 |
| | 3 | −29 | | |
| | 1 | −15 | | |
| 8 | 10 | −35 | 0.17 | |
| | 3 | −31 | | |

TABLE-continued

| Example | Antihypertensive Activity | | α-Adrenergic Receptor Blocking Effect | |
|---|---|---|---|---|
| | Dose mg/kg | % Blood Pressure Change | In Vitro Activity Ratio | In Vivo Activity Ratio |
| 9 | 1 | −13 | 0.19 | |
| | 10 | −41 | | |
| | 3 | −26 | | |
| 10 | 1 | −14 | | |
| | 10 | −25 | | |
| | 3 | −23 | | |
| 11 | 1 | −14 | | |
| | 10 | −33 | | |
| | 3 | −27 | | |
| 12 | 1 | −14 | 0.12 | |
| | 10 | −32 | | |
| | 3 | −24 | | |
| 13 | 1 | −20 | 0.02 | |
| | 10 | −28 | | |
| | 3 | −28 | | |
| 14 | 1 | −19 | 0.10 | |
| | 10 | −33 | | |
| | 3 | −22 | | |
| 15 | 1 | −12 | 0.19 | 0.09 |
| | 10 | −37 | | |
| | 3 | −25 | | |
| 16 | 1 | −20 | 0.35 | |
| | 10 | −28 | | |
| | 3 | −22 | | |
| | 1 | −4 | | |

ISOLATED RAT SEMINAL VESICLE ASSAY

Dangan et al., *Int. j. Neuropharmacol.*, 4:219 (1965) have shown that the seminal vesicle of the rat is a tissue which is notably responsive to compounds which activate α-receptors but is relatively insensitive to compounds which activate β-receptors. Lietch et al., *Brit. J. Pharmacol.*, 9:236 (1954), have employed the isolated rat seminal vesicle in the comparative assay of α-receptor blocking drugs and the present studies were carried out using a modification of their procedure.

Male Long Evans rats weighing approximately 300 g. were sacrificed by a sharp blow on the head. Seminal vesicles were removed and transfered to a shallow dish containing modified Tyrode's solution. The vesicles were emptied of their contents by squeezing them gently with a pair of forceps. Silk thread (4-0) was attached to both ends of the vesicle and it was suspended in a 20 ml. muscle chamber containing modified oxygenated Tyrode's solution (g./liter: NaCl 8, KCl 0.2, $CaCl_2$ 0.26, $NaHCO_3$ 1, $Na_2HPO_4$ 0.575, glucose 0.5 and $MgCl_2$ 0.02). The bathing fluid was maintained at 37° C. with a thermostatically controlled isolated organ tissue bath. Contractions were recorded isometrically by means of a force displacement transducer and recordings were made with a Beckman RP Dynograph. Norepinephrine (NE) was added to the muscle chamber in volumes ranging from 0.1 to 0.4 ml. with a 1 ml. syringe attached to a 3 inch 20 gauge needle. NE and test compounds were dissolved in deionized water.

NE dose response curves were obtained alone and in the presence of test compounds. NE was allowed to remain in contact with the strip until a maximal contraction was obtained. The strip was then washed with the perfusion fluid for 15–30 seconds and the preparation was allowed to return to base line before a subsequent dose of NE was given. Increasing amounts of NE were injected into the bath in the same manner until a complete dose response was obtained.

The seminal vesicles used to obtain the control NE dose response were discarded and new preparations were placed in the tissue bath for evaluation of the test compound. The test compound was added directly to the perfusion fluid (10 nanograms/ml.) and the strips were allowed to remain in contact with the bathing media for at least 10 minutes before the NE dose response was determined. Seminal vesicles from the same rat were used for control and for test drug.

$ED_{50}$ values for NE were obtained by regression analysis as described by Finney, *Probit, Analysis*, 2d Ed., Cambridge (1964). A minimum of 4 strips and at least 4 doses were employed to calculate the regression lines. The ED50 value is defined as the concentration of NE which produces a contraction equal to 50% of the maximal contraction.

The ratio of the α-adrenergic blocking activity of the compounds of this invention, referred to as "compound" in the calculations below, relative to that of prazosin was calculated as follows:

$$\% \text{ Change from NE} = \frac{ED50 \text{ NE} + \text{Drug} - ED50 \text{ NE Alone}}{ED50 \text{ NE Alone}} \times 100$$

The value obtained for the compound was then expressed as a ratio of the value obtained for prazosin.

$$\text{Activity Ratio} = \frac{\% \text{ Change for NE} - \text{Compound}}{\% \text{ Change from NE} - \text{Prazosin}}$$

ANESTHETIZED DOG ASSAY FOR α-ADRENERGIC BLOCKING AGENTS

Nash, C.B., *Pharmacological Research Communications*, 4:423, (1969) and Maxwell, R.A., *Drill's Pharmacology in Medicine*, (1971) p. 683 have shown that in anesthetized dogs α-adrenergic blocking agents antagonize the blood pressure elevating effects of intravenous norepinephrine. Thus, blood pressure responses to norepinephrine (NE) in anesthetized dogs was used as a comparative assay for α-adrenergic receptor blocking properties of drugs.

Experiments were done on mongrel dogs anesthetized with sodium pentobarbital, 30 mg./kg. iv. The left femoral artery was cannulated to record aortic blood pressure and a femoral vein was cannulated for administration of drugs. All animals underwent a bilateral vagotomy. A norepinephrine dose-response curve was obtained by administering increasing doses of iv norepinephrine (0.01 – 1 μg./kg.). The test drug was then administered iv at 3 mg./kg. Approximately 30 minutes later a dose-response curve was again established for iv norepinephrine (0.01–10 μg./kg.). The dose of norepinephrine (with 95% confidence limits) that increased blood pressure by 50 mm. of Hg was obtained from doseresponse curve analysis before and after the compounds of this invention. The ratio of the α-adrenergic blocking activity of the compounds of this invention relative to that of prazosin was obtained as follows:

$$\text{Activity Ratio} = \frac{\frac{\text{ED50 mm Hg}}{\text{Compound of this invention}} - \frac{\text{ED50 mm Hg}}{\text{NE}}}{\frac{\text{ED50 mm Hg}}{\text{Prazosin}} - \frac{\text{ED50 mm Hg}}{\text{NE}}}$$

We claim:
1. A compound having the formula:

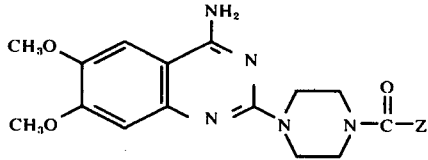

wherein Z is either the radical

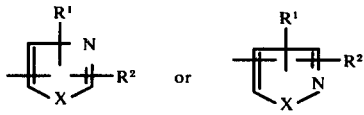

in which X is either oxygen or sulfur and $R^1$ and $R^2$ may be the same or different and are selected from the group consisting of hydrogen, (lower)alkyl having from 1 to 6 carbon atoms, (lower)alkoxy having from 1 to 6 carbon atoms and (lower)alkylthio having from 1 to 6 carbon atoms and pharmaceutically acceptable acid addition salts thereof.

2. A compound of claim 1 in which Z is the radical

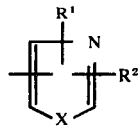

in which X is either oxygen or sulfur and $R^1$ and $R^2$ may be the same or different and are selected from the group consisting of hydrogen, (lower)alkyl having from 1 to 6 carbon atoms, (lower)alkoxy having from 1 to 6 carbon atoms and (lower)alkylthio having from 1 to 6 carbon atoms.

3. A compound of claim 2 in which X is oxygen.
4. A compound of claim 2 in which X is sulfur.
5. A compound of claim 1 in which Z is the radical

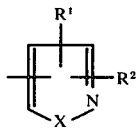

in which X is either oxygen or sulfur and $R^1$ and $R^2$ may be the same or different and are selected from the group consisting of hydrogen, (lower)alkyl having from 1 to 6 carbon atoms, (lower)alkoxy having from 1 to 6 carbon atoms and (lower)alkylthio having from 1 to 6 carbon atoms.

6. A compound of claim 5 in which X is oxygen.
7. A compound of claim 5 in which X is sulfur.
8. A compound of claim 1 being the compound 4-amino-6,7-dimethoxy-2-[4-(oxazole-4-carbonyl)piperazin-1-yl] quinazoline hydrochloride.
9. A compound of claim 1 being the compound 4-amino-6,7-dimethoxy-2-[4-(isothiazole-4-carbonyl)-piperazin-1-yl]quinazoline hydrochloride.
10. A compound of claim 1 being the compound 4-amino-6,7-dimethoxy-2-[4-(2-methylthiazole-4-carbonyl)piperazin-1-yl] quinazoline hydrochloride.
11. A compound of claim 1 being the compound 4-amino-6,7-dimethoxy-2-[4-(2-methylthiazole-5-carbonyl)piperazin-1-yl]quinazoline hydrochloride.
12. A compound of claim 1 being the compound 4-amino-6,7-dimethoxy-2-[4-(5-methylisoxazole-3-carbonyl)piperazin-1-yl]quinazoline hydrochloride.

* * * * *